United States Patent
Nokihara et al.

(10) Patent No.: US 9,778,256 B2
(45) Date of Patent: Oct. 3, 2017

(54) BIOCHIP SUBSTRATE AND BIOCHIP

(75) Inventors: Kiyoshi Nokihara, Kyoto (JP); Yasuo Oka, Fuji (JP)

(73) Assignees: HIPEP LABORATORIES, Kyoto-shi (JP); NIPPON LIGHT METAL COMPANY, LTD., Tokyo (JP)

(*) Notice: Subject to any disclaimer, the term of this patent is extended or adjusted under 35 U.S.C. 154(b) by 2340 days.

(21) Appl. No.: 11/922,108

(22) PCT Filed: Jun. 16, 2006

(86) PCT No.: PCT/JP2006/312119
§ 371 (c)(1),
(2), (4) Date: Dec. 13, 2007

(87) PCT Pub. No.: WO2006/135045
PCT Pub. Date: Dec. 21, 2006

(65) Prior Publication Data
US 2010/0130380 A1 May 27, 2010

(30) Foreign Application Priority Data
Jun. 17, 2005 (JP) ................................. 2005-177466

(51) Int. Cl.
| | |
|---|---|
| C40B 60/14 | (2006.01) |
| G01N 33/543 | (2006.01) |
| B01L 3/00 | (2006.01) |
| B82Y 30/00 | (2011.01) |

(52) U.S. Cl.
CPC ...... G01N 33/54393 (2013.01); B01L 3/5085 (2013.01); B82Y 30/00 (2013.01);
(Continued)

(58) Field of Classification Search
None
See application file for complete search history.

(56) References Cited

U.S. PATENT DOCUMENTS

2002/0090649 A1* 7/2002 Chan et al. .................... 435/7.1
2003/0134267 A1* 7/2003 Kang et al. ...................... 435/4
(Continued)

FOREIGN PATENT DOCUMENTS

| JP | 2003-517149 A | 5/2003 |
| JP | 2003-202343 A | 7/2003 |

(Continued)

OTHER PUBLICATIONS

Young et al. (Monitoring enzymatic reactions in nanoliter wells, 2003, Journal of Microscopy, vol. 212, pp. 254-263).*
(Continued)

*Primary Examiner* — Christian Boesen
(74) *Attorney, Agent, or Firm* — Birch, Stewart, Kolasch & Birch, LLP

(57) ABSTRACT

A biochip substrate which is free from cross-contamination due to spot spreading or contact with spots adjacent to each other, and a biochip using the same. A biochip substrate on which multiple valleys for immobilizing biological substances are formed so as to prevent cross-contamination due to spot spreading or contact with spots adjacent to each other, and a biochip using the same are provided. Moreover, it is found out that a desired binding in a target molecule contained in a test sample occurs at a detectable level in a solution system even in the case where a valley have such a small capacity as 1 nL to 10 nL.

10 Claims, 2 Drawing Sheets

(52) U.S. Cl.
CPC ... *B01L 2200/12* (2013.01); *B01L 2300/0636* (2013.01); *B01L 2300/0829* (2013.01); *B01L 2300/0893* (2013.01); *B01L 2300/0896* (2013.01); *B01L 2300/12* (2013.01); *C40B 60/14* (2013.01)

(56) References Cited

U.S. PATENT DOCUMENTS

2004/0245209 A1* 12/2004 Jung et al. .................. 216/8
2005/0046758 A1   3/2005 Matsushita et al.
2006/0121473 A1*  6/2006 Tanga et al. ................ 435/6

FOREIGN PATENT DOCUMENTS

| | | | |
|---|---|---|---|
| JP | 2004-226384 A | | 8/2004 |
| JP | 2005-017073 A | | 1/2005 |
| JP | 2005-043312 | * | 2/2005 |
| JP | 2005-043312 A | | 2/2005 |
| JP | 2005-049101 A | | 2/2005 |
| WO | WO 98/22541 | * | 5/1998 |
| WO | WO 2004/019025 | * | 3/2004 |

OTHER PUBLICATIONS

Tanga et al., JP 2005/043312, English translation, 18 pages, Feb. 2005.*

* cited by examiner

BIOCHIP SUBSTRATE AND BIOCHIP

TECHNICAL FIELD

The present invention relates to a biochip on which a biologically relevant substance(s) such as nucleic acids, peptides, sugars and the like is(are) immobilized, as well as to a substrate therefor.

BACKGROUND ART

It is well known that biochips having a flat substrate surface on which DNAs or proteins are immobilized include those prepared by Affymetrix method in which oligonucleotides are synthesized on the surface of the substrate using photolithography, and those prepared by Stanford method in which preliminarily provided probe DNAs or probe proteins are spotted so as to immobilize them on the surface of the substrate. Either type of the biochips is used such that fluorescence is detected after biological reactions with a target, and identification of the molecule or diagnosis is performed from the resulted pattern.

Among the above-mentioned two methods, the Affymetrix method has a drawback in that stable immobilization and synthesis of a long oligonucleotide are difficult because the oligonucleotide is synthesized on the surface of the substrate, and that the cost is also high. On the other hand, in the Stanford method, in order to place small spots of probe DNAs, probe proteins and the like are placed on the surface of the substrate and to immobilize the molecules to be recognized by adsorption or covalent bonds, amino groups, aldehyde groups, silanol groups or epoxy groups are covalently attached to, or polylysine is noncovalently attached to the surface of the substrate. However, it is known that since these functional groups or the polylysine are attached to the entire surface of the substrate, spots may be diffused, cross-contamination may occur due to contacts between adjacent spots, and the amounts of the immobilized molecules may differ when some spotting methods are used. It is true that uniformity in the amount and the shape (e.g., the diameter of the spots) of the spots is not attained due to the properties of the molecules per se, such as the hydrophobicity and ease of ionization thereof. In recent years, DNA chips are widespread and most of them use a glass as the material of the substrate. However, the amount of the molecules which can be bound by the modification of the silanol groups on the surface of the glass is small, and when a slide glass, a generally used substrate, is used, the amount is several nanomoles, so that the capacity of the substrate to immobilize the molecules is low. In case of immobilizing the molecules by adsorption, there is also a drawback in that non-specific adsorption strongly occurs, so that the fluorescent substances in unreacted areas, which remain even after washing after the biological reactions, decrease the S/N ratio of the detection.

Patent Literature 1: JP 2001-128683 A
Patent Literature 2: Japanese Translated PCT Patent Application Laid-open No. 2005-510440

DISCLOSURE OF THE INVENTION

Problems which the Invention Tries to Solve

An object of the present invention is to provide a substrate for biochips with which spots are not diffused and cross-contamination due to contacts between adjacent spots does not occur.

Means for Solving the Problems

After intensive study, the present inventors inferred that a substrate for biochips with which spots are not diffused and cross-contamination due to contacts between adjacent spots does not occur may be provided by forming a plurality of recesses therein for immobilizing a biologically relevant substance(s), thereby completing the present invention.

That is, the present invention provides a substrate for biochips, which substrate has a plurality of recesses formed therein for immobilizing a biologically relevant substance(s). The present invention also provides a biochip comprising the substrate according to the present invention, and a biologically relevant substance immobilized on the substrate. The present invention further provides a method of producing a biochip, the method comprising the steps of providing the substrate for biochips, according to the present invention; and immobilizing a biologically relevant substance(s) on the substrate. The present invention still further provides use of the substrate for biochips, according to the present invention, for the production of a substrate for biochips.

Effects of the Invention

By the present invention, a substrate for biochips and a biochip using the substrate, with which spots are not diffused and cross-contamination due to contacts between adjacent spots does not occur, were provided.

BEST MODE FOR CARRYING OUT THE INVENTION

Figure 1:
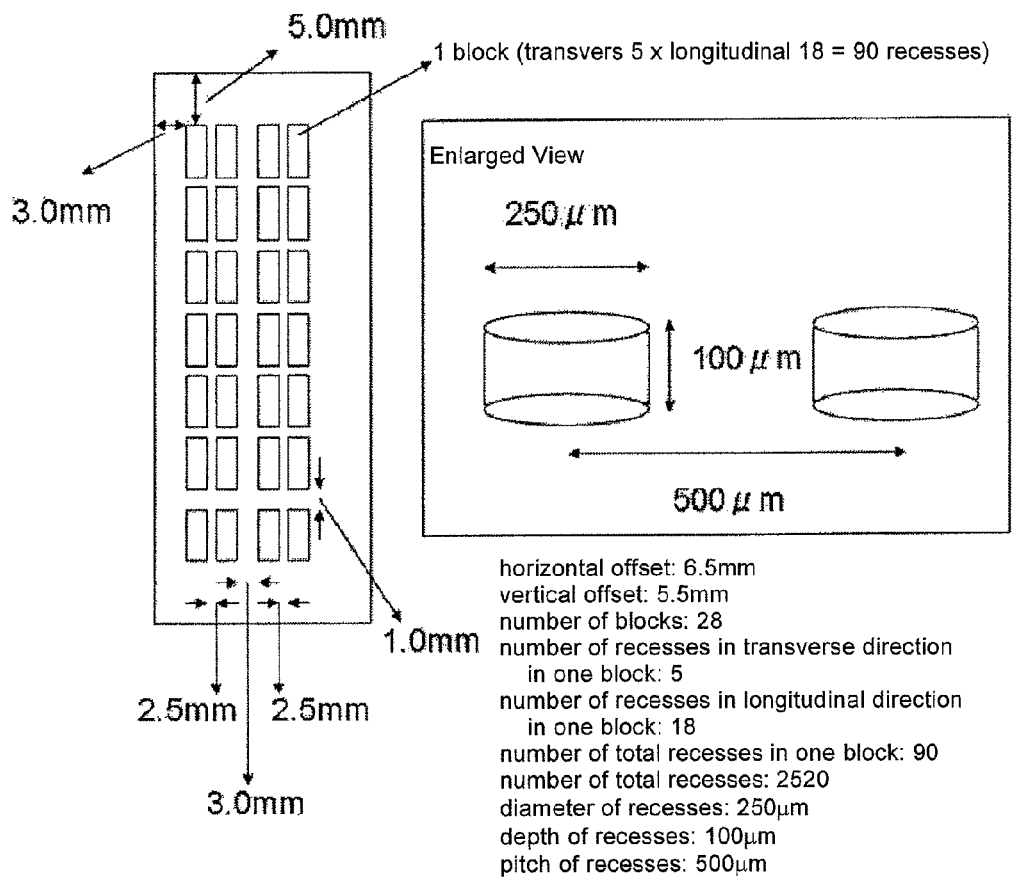
FIG. 1 shows an arrangement of the recesses formed in the substrate prepared in an Example of the present invention.

As described above, the substrate for biochips according to the present invention has a plurality of recesses for immobilizing a biologically relevant substance(s). The number of the recesses per one substrate is not restricted, and it is usually about 100 to 50,000, preferably about 1000 to 10,000 per one substrate having a size of a slide glass. The volume of each recess is not restricted, and is preferably 1 nL to 10 nL. The fact that the desired binding of the target molecules in a test sample occurs at a detectable level in solution systems even if the volume of each recess is so small as mentioned above was not known, and was first discovered by the present invention. Since the volume of each recess is small, the amount of the test sample subjected to the reaction is also small, which is advantageous because the volume of the valuable test sample can be made small. The volume of each well in a microplate, in which binding reactions are carried out in solution systems is 200 µL, to 300 µL. Thus, the present inventors first discovered that the desired binding of target molecules in a test sample can be detected in solution systems in a volume of $\frac{1}{10,000}$ or less of the well of a microplate. Although the size of each recess is not restricted, when the shape of the recess is cylindrical, one having a diameter of 50 μm to 350 μm, and a depth of about 10 μm to 200 μm, which gives a volume of the above-described about 1 nL to 10 nL is preferred. Although the shape of the recess is not restricted at all, cylindrical one is preferred from the viewpoint of ease of production.

The inner wall (including the bottom) of the recess is preferably made of carbon such as graphite, diamond, diamond-like carbon or amorphous carbon. To such a carbon, functional groups useful for immobilizing the biological substances can be bound easily at a high density by the methods described below.

In a preferred mode in which the inner wall of the recess is made of carbon, the substrate is made of a metal, and a carbon layer such as one made of graphite, diamond, diamond-like carbon or amorphous carbon is formed only in the inside of the recess. In this case, as the metal for constituting the substrate, a metal selected from the group consisting of aluminum, titanium, stainless steel and an alloy containing at least one of these metals is preferred because of the reasons that these metals are easy to work, excellent in flatness because they are rigid, excellent in smoothness after polishing because the surface hardness is high, and so on.

If the surface of the substrate body made of a metal is bent or irregular, diffuse reflection is increased or the focusing in the detection cannot be attained, so that the S/N ratio in the detection is decreased. Therefore, the substrate body is preferably flat and its surface is preferably smooth. Therefore, it is preferred to anneal the substrate body under pressure to eliminate the strain and to promote the flatness after sizing such as punching, and, after grinding the surface to make it smooth, to increase the surface precision by further polishing the surface. These workings for attaining flatness and smoothness can be carried out by conventional metal working methods. In cases where the metal is aluminum or an aluminum alloy, since it is difficult to secure surface precision because the metal is soft, it is preferred to perform a hardening treatment such as electroless NiP plating or anodic oxidation. The surface roughness Ra of the substrate body is preferably less than 1 nm. Although the lower limit of Ra is not restricted, about 0.2 nm is usually close to the limit of working precision. The surface flatness of the substrate body is preferably less than 5 μm. The thickness of the substrate body is not restricted, and is usually about 0.5 mm to 2 mm. In cases where the substrate body is made of aluminum or an aluminum alloy, and a plated layer of NiP or the like is formed on the substrate body, or an oxide layer is formed on the substrate body by anodic oxidation of the surface, the thickness of the plated layer or the oxide layer is not restricted and is usually about 5 μm to 30 μm.

The recesses can be formed in the substrate made of a metal by mechanical processing using a microdrill; laser processing using carbon dioxide laser, YAG laser, excimer laser or the like; energy radiation processing using focused ion beam or the like; lithography processing; press working or the like.

In cases where a carbon layer is formed in the inside of each recess in the substrate made of a metal, the carbon layer is a layer made of carbon such as graphite, diamond, diamond-like carbon or amorphous carbon, and can be formed by sputtering method, vapor deposition method, CVD (chemical vapor deposition method) or the like. That is, the graphite layer can be formed by, for example, vacuum vapor deposition method using graphite particles as a vapor deposition source. The diamond layer can be formed by, for example, low pressure gas-phase synthesis method using a CVD apparatus having a heat filament. The diamond-like carbon can be formed by, for example, ion-sputtering method or high frequency plasma CVD method. Amorphous carbon can be formed by, for example, high frequency sputtering method. These methods can easily be carried out using commercially available apparatuses. As described above, in cases where the plated layer or oxide layer is formed, the carbon layer is formed thereon. That is, the carbon layer is formed on the surface of the substrate body indirectly through another layer.

In cases where the carbon layer is formed in the inside of each recess in the substrate made of a metal, it is preferred that the carbon layer be formed only in the inside of each recess and be not formed on the substrate surface between the recesses. As described below, functional groups for immobilizing the biologically relevant substance(s) can be bound to the carbon layer. If the carbon layer is formed only in the inside of each recess and is not formed on the substrate surface between the recesses, the functional groups bound to the carbon layer also exist only in the recesses, so that it is assured that the biologically relevant substance(s) be immobilized only in the recesses. Forming the carbon layer only in the recesses can be attained by, for example, forming the carbon layer on the entire surface of the substrate by the above-described sputtering method, vapor deposition method, CVD method or the like, and then removing the carbon layer formed on the substrate surface between the recesses by grinding the carbon layer. By this method, the carbon layer can be easily formed only in the inside of the small recesses.

Another preferred method for forming the inner wall of the recesses with carbon is to make the entire substrate with carbon. By forming the substrate itself with carbon such as graphite or amorphous carbon, the inner wall of the recesses can be formed with carbon. In this case, the recesses can be formed by mechanical processing using a microdrill; laser processing using carbon dioxide laser, YAG laser, excimer laser or the like; energy radiation processing using focused ion beam or the like; lithography processing; injection molding; stamping with a number of hard needles, or the like. Even in cases where the entire substrate is made of carbon, the substrate surface is preferably flat, and preferably has a surface roughness within the range described above for the substrates made of a metal. Such a surface roughness can be attained by grinding the surface with a commercially available grinder. The grinding is performed after attaching the functional groups on the entire substrate to remove the functional groups formed on the substrate surface between the recesses.

The carbon constituting the inner wall of the recesses preferably has functional groups for immobilizing the biologically relevant substance(s). The functional groups can be provided by binding the functional groups to the carbon material constituting the inner wall of the recesses. Examples of the functional groups include, but not limited to, amino group, aldehyde group, carboxyl group, sulfhydryl group and epoxy group. Among these groups, amino group is especially preferred because it is versatile and binding with biologically relevant substances is easy. These functional groups to be covalently bound to the carbon can be covalently bound to the carbon by cleaving C—C bond, C═C bond and/or C—O bond of the carbon by irradiation with plasma or ultraviolet light, and binding the resulting carbon radical with the functional groups or a compound(s) having the functional groups. For example, amino groups can be, as will be described in detail later in the Examples below, covalently bound to carbon by converting the oxygen in the air to ozone and reacting the resulting ozone with the carbon by irradiating the carbon layer with ultraviolet light in the air, then after evacuation, reacting chlorine gas with the resultant to chlorinate the carbon, and, after evacuation, reacting ammonia gas with the resultant to aminate the carbon. Alternatively, amino groups can also be directly introduced by irradiation with ammonia plasma. Still alternatively, amino groups can be generated on the surface by generating radicals by irradiating the substrate surface with argon plasma, converting the radicals to peroxide by air oxidation, and by reacting the resulting peroxide with allylamine or the like. Aldehyde groups can be obtained by, for example, converting the surface of the carbon to an acid chloride, and reducing the resulting acid chloride. Carboxyl groups may be obtained by, for example, converting amino groups to diazonium ions, converting the resulting diazonium ions to nitrile, and hydrolyzing the resulting nitrile. Carboxyl groups can also be obtained by oxidizing alkyl groups with potassium permanganate or the like. Sulfhydryl groups can be obtained by, for example, halogenating the surface of the carbon with light or the like, and reacting the generated halogenated alkyl with a thiol. Epoxy groups may be generated by treating the carbon-carbon double bonds with a peracid. Any of these reactions may be carried out based on the reactions in the field of organic synthetic chemistry, which are well-known by those skilled in the art. The functional groups are not necessarily bound to carbon by covalent bonds, but a compound(s) having the functional group(s) can be noncovalently attached by physical adsorption. For example, amino groups may be given to the carbon layer by physically adsorbing poly-lysine to the carbon layer, which poly-lysine is obtained by polycondensation of lysine which is an amino acid having an amino group in its side chain. The density of the functional groups given to the carbon layer is not restricted, and usually about 10 pmol to 1000 pmol, preferably about 100 pmol to 300 pmol per 1 $cm^2$ of the carbon layer.

By immobilization of a biologically relevant substance(s) to the recesses of the above-described substrate for biochips, according to the present invention, a biochip can be obtained. Examples of the biologically relevant substances include nucleic acids such as DNAs and RNAs; various proteins, antibodies, enzymes and synthetic and natural peptides; saccharides such as polysaccharides and oligosaccharides; various lipids; and complexes thereof (glycoproteins, glycolipids, lipoproteins and the like). Further, cells can also be immobilized, so that the cell is also included within the scope of the term "biologically relevant substance". Still further, low molecular compounds such as coenzymes, antigen epitopes and haptens are also included within the scope of the term "biologically relevant substance" because they specifically interact with biopolymers such as enzymes and antibodies. These biologically relevant substances may be bound to the above-described carbon layer as they are, or they may be bound to the above-described carbon layer in the state of being immobilized to other carriers such as plastic beads.

Immobilization of the biologically relevant substance(s) to the carbon material having the functional groups may be carried out by well-known methods through the above-described functional groups. For example, in cases where the functional groups are amino groups, as will be described in detail in the Examples below, biologically relevant substances may be immobilized to the substrate by converting the amino groups to the corresponding anhydride with bromoacetic acid and carbodiimide; reacting the resultant with amino groups to bromoacetylate the surface; and reacting the resultant with sulfhydryl groups in the biologically relevant substances such as peptides. Alternatively, the biologically relevant substances can be immobilized through glutaraldehyde by reacting the amino groups with the amino groups in the biologically relevant molecules. In cases where the functional groups are aldehyde groups, immobilization of the biomolecules desired to be immobilized can be attained by the reaction with the amino groups in the biomolecules. In cases where the functional groups are carboxyl groups, an ester is formed with N-hydroxysuccinimide, and the resulting ester can be bound with the amino groups in the biologically relevant substances. In cases where the functional groups are sulfhydryl groups, immobilization may be attained by selectively bromoacetylating the amino groups in the biologically relevant molecules. Alternatively, immobilization may be attained by binding the sulfhydryl groups with other sulfhydryl groups through disulfides. Further, sulfhydryl groups can be bound by selectively converting the amino groups at the site to be subjected to the immobilization to maleimide, and binding the resultant with the sulfhydryl groups (for example, N-6 maleimide caproic acid is condensed with the amino groups). In cases where the functional groups are epoxy groups, the biologically relevant substances may be immobilized, similarly, by reaction of the epoxy groups with biologically relevant substance having maleimides.

Not only in cases where, needless to say, the inner wall of the recesses does not have the functional groups, but also in cases where the inner wall of the recesses have the functional groups, it is not necessary to immobilize the biologically relevant substance(s) by covalent bonds (see Example 3 below). By simply placing a solution(s) of the biologically relevant substance(s) to the recesses, and drying the solution(s) to adhere the biologically relevant substance(s) in the recesses, the substrate can be used as a biochip. In this case, a biologically relevant substance(s) which change(s) its(their) fluorescence or the like by binding with a target substance(s) is(are) placed in the recesses. By using such a dry type biochip, a small amount of a test sample can be detected simply. Unlike the measurements in a solution, by performing the measurements after drying the solution to be measured, and by drying the solution of a biologically relevant substance(s) which is a test solution, the chip can be transported and stored. Further, when carrying out the measurement, by drying the substrate after performing the binding reaction between the biologically relevant substance(s) dissolved by adding a test sample solution, and performing the measurement, a simple measurement method with which the evaporation of the small amount of solution is not cared can be realized. Still further, the substrate may be reused.

The present invention will now be described more concretely by way of examples. However, the present invention is not restricted to the Examples.

Example 1

1. Production of Substrate for Biochips (Part 1)

A high purity Al—Mg alloy plate (Mg content: 4% by weight) with a thickness of 1.2 mm was sized to 26 mm×76 mm by punching with a press. A plurality of the plates were stacked and annealed under pressure under an atmosphere at 340° C., thereby removing strain and attaining a flatness of not more than 5 µm. Thereafter, working of the end faces and chamfer (specifically, angle 45°, a length: 0.2 mm) was performed to prepare plates with a size of 25 mm×75 mm.

Then each plate was ground with a double side grinding machine 16B produced by SpeedFam, in which a sponge grindstone was mounted, to attain a thickness of 0.98 mm and a degree of parallelization of not more than 1 µm. Then micro recesses with a size shown in FIG. 1 were formed in the substrate by mechanical processing with a microdrill using a marking press CAMM-3 produced by Roland. The resulting plate was then subjected to, in the order mentioned, degreasing, etching, acid activation, and zincate treatments. More particularly, the plate was sequentially immersed in alkaline degreasing liquid AD-68F (50° C.) produced by Uyemura for 5 minutes, in sulfuric acid-phosphoric acid etching liquid AD-101F (80° C.) for 2 minutes, in nitric acid activating liquid (20° C.) for 1 minute, and in zincate liquid AD-301F3X (20° C.) for 30 seconds, thereby carrying out pretreatments. Thereafter, the plate was immersed in electroless NiP liquid NI-422 (90° C.) produced by Meltex Corporation for 2 hours to form a plated layer on both sides of the plate, each of which had a thickness of 12 µm. Each of the plated layers was polished by 2 µm with a double side polishing machine 16B produced by SpeedFam using colloidal silica abrasive to obtain a plate having ultrasmooth surfaces. The plate had a thickness of 1.00 mm and a surface roughness Ra of 0.35 nm. The flatness, degree of parallelization and Ra were measured using a flat meter FT-SOLD produced by Mizojiri, roundness measuring machine Talyrond produced by Rank Taylor Hobson and stylus-type surface roughness meter Talystep produced by Rank Taylor Hobson, respectively.

An amorphous carbon layer was then formed on one surface of the plate using high frequency sputtering apparatus CFS-8EP produced by Tokuda Seisakusho. Particularly, sputtering was carried out for 5 minutes under Ar atmosphere at 1.0 Pa, with a feed traveling wave power (Pf) of 1 kW, and with a reflected wave power (Pr) of 20 W. Thereafter, the surface was polished with a double side polishing machine 16B produced by SpeedFam using colloidal silica abrasive to remove the functional groups other than the inner wall of the recesses. Then functional groups were given to the thus formed amorphous carbon layer in the micro recesses. The functional groups were given by the following method: First, the substrate was set in a stainless steel vessel having a window made of a synthetic quartz, and irradiated with an ultraviolet lamp (lamp output power: 110 W) from a distance of 3 cm, which lamp emits an ultraviolet light having a component with a wavelength of 185 nm at 30% intensity and a component with a wavelength of 254 nm at 100% intensity, thereby subjecting the surface of the substrate to an ozone treatment. After evacuation, chlorine was then introduced to perform chlorine treatment (25° C., 5 minutes) under chlorine atmosphere at 13 Pa. Further, after evacuation, ammonia was introduced and amination treatment (25° C., 5 minutes) was carried out under ammonia atmosphere at 13 Pa. The amount of the amino groups on the substrate was 4.1 nmol/both surfaces. The amount of the amino groups was measured by a method in which the surfaces of the substrate were treated with hydrochloric acid and then the remaining hydrochloric acid was back titrated with aqueous sodium hydroxide solution (Japanese Patent Application No. 2005-069554).

Example 2

2. Production of Substrate for Biochips (Part 2)

After placing a thermosetting phenol resin in a mold, a two-step heat treatment at 90° C. and 120° C. was performed to prepare a Bakelite block. A plate having a thickness of 2 mm and a size of 31 mm×95 mm was cut out from the block, and was ground with a double side polishing machine 16B produced by SpeedFam, in which an iron surface plate was mounted, to attain a thickness of 1.30 mm and a degree of parallelization of not more than 1 µm. After chamfering, the resulting plate was slowly heated to 1200° C. thereby carbonizing the substrate to amorphous carbon. Thereafter, using a LD-excited YVO4 laser produced by Fuji Electric, the small recesses having the size shown in FIG. 1 were formed in the air, and then functional groups were attached by the following method: First, the substrate was set in a stainless steel vessel having a window made of a synthetic quartz, and irradiated with an ultraviolet lamp (lamp output power: 110 W) from a distance of 3 cm, which lamp emits an ultraviolet light having a component with a wavelength of 185 nm at 30% intensity and a component with a wavelength of 254 nm at 100% intensity, thereby subjecting the surface of the substrate to an ozone treatment. After evacuation, chlorine was then introduced to perform chlorine treatment (25° C., 5 minutes) under chlorine atmosphere at 13 Pa. Further, after evacuation, ammonia was introduced and amination treatment (25° C., 5 minutes) was carried out under ammonia atmosphere at 13 Pa. The amount of the amino groups on the substrate was 4.1 nmol/both surfaces. The amount of the amino groups was measured by a method in which the surfaces of the substrate were treated with hydrochloric acid and then the remaining hydrochloric acid was back titrated with aqueous sodium hydroxide solution (Japanese Patent Application No. 2005-069554). The surface of the resulting substrate was polished with a double side polishing machine 16B produced by SpeedFam using colloidal silica abrasive to remove the functional groups other than only the inner wall of the recesses, thereby preparing a selectively adsorptive amorphous carbon substrate.

Example 3

Calmodulin was measured using a peptide chip having recesses in which a peptide having α-helix structure was immobilized, which peptide was labeled with different fluorescence labels at its both ends. More specifically, this was carried out as follows:

The sequence of the core region of the peptide having α-helix structure was designed by molecular modeling using a computer (molecular modeling using Insight II/Discover of Molecular Simulation, U.S.) based on the amino acid sequence of the peptide described in a reference (K. T. O'Neil and W. F. DeGrado, Trend Biochem Sci, 15, 59-64 (1990)). As a result, the designed amino acid sequence of the core region was Leu-Lys-Lys-Leu-Leu-Lys-Leu-Leu-Lys-Lys-Leu-Leu-Lys-Leu (SEQ ID NO:1). This sequence is known to specifically bind to calmodulin. To this sequence, a Cys residue as an anchor for immobilization, and as fluorescently labeled residues, Lys(TAMRA) and Lys(FAM) were added. Thus, an amino acid sequence Cys-Lys(TAMRA)-Leu-Lys-Lys-Leu-Leu-Lys-Leu-Leu-Lys-Lys-Leu-Leu-Lys-Leu-Lys(FAM)-NH$_2$ (SEQ ID NO:2) was synthesized. Fluorescent amino acid derivatives were prepared by introducing a fluorescent group to the side chain of lysine, and were used as building blocks for the synthesis. That is, the fluorescently modified amino acid derivatives were converted to N-hydroxysuccinimide active ester derivatives using diisopropylcarbidiimide. The amino group in the side chain of Fmoc-Lys-OH (Novabiochem, Switzerland, Product No. 04-12-1042) and the above-described active ester were reacted by a conventional method in dimethylformamide overnight at room temperature with stirring, and then the reaction mixture was concentrated and subjected to precipitation with ether to obtain Fmoc-Lys (TAMRA)-OH. Yield: 80%. (Fmoc: fluorenyl-methylcarbonyl). In the similar manner, Fmoc-Lys(FAM)-OH was obtained. Yield: 85%

Figure 2:
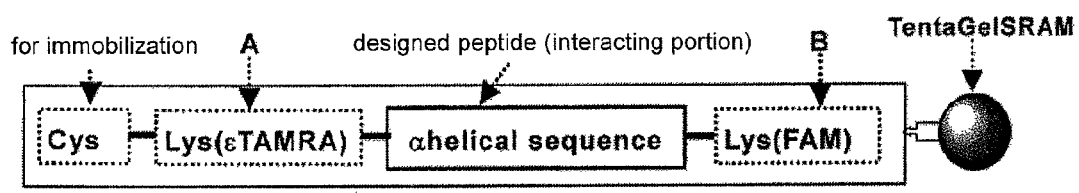
FIG. 2 shows the structure of the peptide prepared in an Example of the present invention.

By using these fluorescent derivatives as building blocks, the synthetic peptide shown in FIG. 2 having the labels A and B was synthesized by the conventional solid phase peptide synthesis by Fmoc method in a scale of 15 micromoles each. That is, Fmoc-amino acid derivatives were sequentially polycondensed using TentaGel SRAM, Rapp Polymere, Germany, Product No.: S30-023 (Rink amide resin with polyethylene glycol chain) as the solid support. More specifically, the synthesis was carried out by the method described in Japanese Patent No. 2007165 directed to a multiple product chemical reaction apparatus, using a commercially available multiple peptide synthesizer, Model PSSM-8, Shimadzu Corporation.

The synthesized labeled peptide was dissolved in 60% DMF to a concentration of 1.0 and the obtained solution was placed in each recess in the substrate prepared in Example 1 or Example 2 using SpotBot (TeleChem International, U.S.) in an amount of 1.8 nL per recess, thereby placing the fluorescently labeled α-peptide (the substance to be recognized) in the recesses. In this case, the peptide was not immobilized. After adding the peptide solution to each recess and drying the solution, quantification of the binding (recognition) was tried. Calmodulin was dissolved in a solution containing 20 mM Tris-HCl, 100 μM $CaCl_2$, 150 mM NaCl and 20 mM PEG2000, and the resulting solution was placed in each recess in an amount of 3.9 nL (0.5 mg/mL) per recess. The substrate was incubated at 25° C. and immediately the measurement with a fluorescent scanner (CRBIO IIe produced by Hitachi Soft Engineering) was carried out (excitation wavelength: 498 nm, measurement wavelength: 579 nm).

Figure 3:
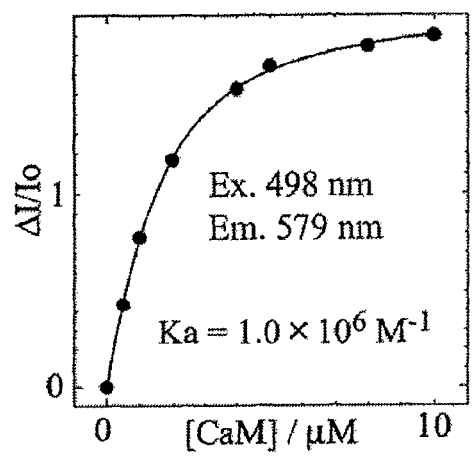
FIG. 3 shows the relationship between the concentration of calmodulin and fluorescence intensity measured in Example 3 of the present invention.

The results of the measurement on the substrate prepared in Example 1 are shown in FIG. 3. The fluorescence changed depending on the calmodulin concentration, so that it was proved that quantification of calmodulin can be attained using this biochip. Similar results were obtained also when the substrate of Example 2 was used.

Example 4

As the peptide to be immobilized to the functional groups on the carbon layer in the recesses of the biochip prepared in Example 1, a fluorescently labeled peptide having the following sequence was chemically synthesized:

```
                                            (SEQ ID NO: 3)
Ac-Cys-Gly-Lys(FAM)-Gly-Leu-Lys-Lys-Leu-Leu-Lys-

Leu-Leu-Lys-Lys-Leu-Leu-Lys-Leu-Lys(TAMRA)-Gly-

NH2.
```

The fact that this peptide has α-helix structure was confirmed by CD spectrum. Here, both "FAM" and "TAMRA" are fluorescent dyes. When FAM is excited with light, the excitation energy of FAM is transferred to TAMRA depending on the distance between FAM and TAMRA, and TAMRA emits fluorescence (called fluorescence resonance energy transfer, FRET-fluorescence). When a protein binds to the peptide, the helix structure of the peptide is fixed, so that FRET florescence is increased. FRET is a phenomenon that energy is transferred from a donor molecule (FAM in this case) in the excited state to an acceptor molecule (TAMRA in this case) in the ground state, and fluorescence from the acceptor is observed. The peptide is known to specifically bind to calmodulin (CaM). Upon binding to CaM, the distance between FAM and TAMRA is decreased. The larger the amount of CaM, the higher the measured fluorescence intensity from TAMRA, so that the binding can be quantified.

The above-described labeled peptide was dissolved in 60% dimethylformamide (DMF) to a concentration of 2 μM. On the other hand, the amino groups on the substrate prepared in Example 1 were bromoacetylated. Specifically, this was carried out as follows: Bromoacetic acid (BrAcOH, Tokyo Chemical Industry, Mw=138.95, 2.00 mmol, 278 mg) and dicyclohexylcarbodiimide (DCC) (Aldrich Mw=206.33, 1.00 mmol, 206 mg) were dissolved in tetrahydrofuran (3.33 ml), and the resulting solution was gently shaken at room temperature for 60 minutes to form bromoacetic anhydride. The generated insoluble urea was removed by filtration. The resulting aminated substrate was immersed in 5% solution of diisopropylethylamine in NMP and lightly rinsed. The filtrate obtained above was added to this substrate and the substrate was immersed therein at room temperature for 1 hour while lightly shaking the substrate sometimes, thereby attaining bromination. The resulted substrate was washed with ultrapure water (Milli-Q water (trademark)), and dried under nitrogen. The above-described labeled peptide solution was spotted on the substrate to react the peptide with the above-described bromoacetylated amino groups, thereby to immobilize the peptide on the substrate. The spotting was carried out using SpotBot apparatus produced by TeleChem International (California, U.S.) and using a microspotting pin also produced by TeleChem International.

To the thus prepared labeled peptide-immobilized substrate, solutions containing different amounts of CaM (CaM was dissolved in 100 μM calcium chloride solution) were applied, and fluorescence was measured using a scanner (CRBIO IIe produced by Hitachi Software Engineering).

Figure 4:
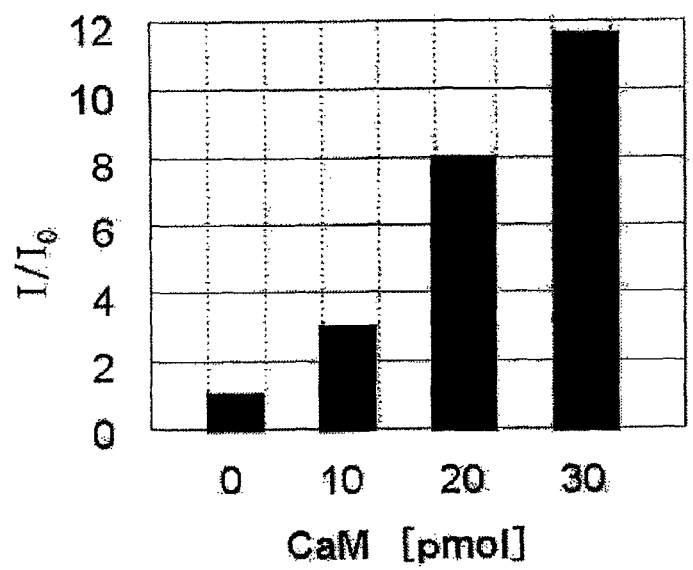
FIG. 4 shows the relationship between the concentration of calmodulin and fluorescence intensity measured in Example 4 of the present invention.

The results are shown in FIG. 4. As shown in FIG. 4, the measured fluorescence intensity increased dependently on the amount of CaM. Thus, it was proved that a substance which specifically reacts with the biologically relevant substance immobilized on the chip can be quantified by the biochip according to the present invention.

Example 5

Three milligrams of (N-(6-maleimidocaproyloxy)succinimide)) produced by Dojin (hereinafter referred to as "EMCS") was weighed, and dissolved in a 2:4:4 mixed solution of dimethylsulfoxide (DMSO)/dimethylformamide (DMF)/dioxane to a final concentration of 0.3 mg/mL, thereby preparing an EMCS solution. The aminated substrate was immersed in this solution at room temperature for 30 minutes, thereby allowing reaction between the amino groups and EMCS active ester. The substrate was then washed with ethanol to remove the unreacted EMCS and reaction side products. Then the substrate was dried under a nitrogen atmosphere to prepare a modified substrate in which only the inside of the microwells was maleimidated.

A peptide having α-helix structure labeled with a fluorescent group TAMRA alone Ac-Cys-Gly-Lys-Lys-Leu-Leu-Lys-Leu-Leu-Lys-Lys-Leu-Leu-Lys-Leu-Lys (TAMRA)-Gly-$NH_2$ (SEQ ID NO:4) was synthesized by a conventional method. When a protein binds to this peptide, the helix structure is changed, and fluorescence intensity is changed accordingly. This peptide is known to specifically binds to calmodulin (CaM) which is a protein, and the larger the amount of CaM, the higher the fluorescence intensity of TAMRA measured, so that CaM can be quantified.

The peptide was dissolved in DMF/pH8.0, 10 mM Tris-HCl (1:1) to a final concentration of 2.0 μM. This peptide solution in an amount of 3.9 nL was added to the substrate using SpotBot produced by TeleChem International (California, U.S.) and using a microspotting pin also produced by TeleChem International. By leaving the substrate to stand for 30 minutes, the maleimide groups and the thiol groups in the cystein of the peptide reacted and the peptide was immobilized. The substrate was washed with DMF/water (1:1).

Solutions containing different amounts of CaM (CaM was dissolved in 100 μM calcium chloride solution) was added to each micro recess in an amount of 3.9 nL per recess using SpotBot produced by TeleChem International (California, U.S). After washing the substrate with Milli-Q water (trade name), fluorescence intensity was measured using a scanner (CRBIO IIe produced by Hitachi Soft Engineering).

The results shown in FIG. 3 were obtained. Thus, the measured fluorescence intensity changed depending on the amount of CaM added to the substrate, so that it was proved that substances which specifically react with the biologically relevant substance immobilized on the chip can be quantified by the biochip of the present invention.

The invention claimed is:

1. A substrate for biochips, which substrate has a plurality of recesses formed therein for immobilizing a biologically relevant substance(s), each of said recess having a volume of 1 nL to 10 nL, each of said recess having an inner wall and a bottom made of carbon, wherein functional groups for immobilizing the biologically relevant substance(s) are bonded only to the carbon of the inner wall and the bottom, and wherein the biologically relevant substance(s) are immobilized to the inner wall and the bottom of the substrate without spots that are diffused and without cross-contamination due to contacts between adjacent spots.

2. The substrate according to claim 1, wherein said substrate is made of a metal and a carbon layer is formed only in the inside of each of said recesses.

3. The substrate according to claim 2, wherein said metal is selected from the group consisting of aluminum, titanium, stainless steel and alloys containing at least one of the metals mentioned.

4. The substrate according to claim 3, wherein said metal is aluminum or an alloy thereof, and a plated layer or a layer of oxide of said metal is formed between said substrate and said carbon layer.

5. The substrate according to any one of claims 2 to 4, wherein said carbon layer is made of graphite, diamond, diamond-like carbon or amorphous carbon.

6. The substrate according to claim 1, wherein said substrate is made of carbon.

7. The substrate according to claim 6, wherein said substrate is made of graphite or amorphous carbon.

8. The substrate according to claim 1, wherein said functional groups are amino groups, aldehyde groups, carboxyl groups, sulfhydryl groups or epoxy groups, or polylysine non-covalently bound to said carbon layer.

9. A biochip comprising said substrate according to claim 1, and a biologically relevant substance(s) immobilized on said substrate.

10. A method of producing a biochip, said method comprising the steps of providing said substrate for biochips, according to claim 1; and immobilizing a biologically relevant substance(s) on said substrate.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide used for binding assay

<400> SEQUENCE: 1

Leu Lys Lys Leu Leu Lys Leu Leu Lys Lys Leu Leu Lys Leu
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic peptide used for binding assay

<400> SEQUENCE: 2

Cys Lys Leu Lys Lys Leu Leu Lys Leu Leu Lys Lys Leu Leu Lys Leu
1               5                   10                  15

Lys

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide used for binding assay

<400> SEQUENCE: 3

Cys Gly Lys Gly Leu Lys Lys Leu Leu Lys Leu Leu Lys Lys Leu Leu
1               5                   10                  15

Lys Leu Lys Gly
            20

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide used for binding assay

<400> SEQUENCE: 4

Cys Gly Leu Lys Lys Leu Leu Lys Leu Leu Lys Lys Leu Leu Lys Leu
1               5                   10                  15

Lys Gly
```